United States Patent
Shedlov

(10) Patent No.: US 6,874,789 B2
(45) Date of Patent: Apr. 5, 2005

(54) LOW MASS ROTARY MOTOR ASSEMBLY

(75) Inventor: Matthew Shedlov, Rockford, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 188 days.

(21) Appl. No.: 10/205,878

(22) Filed: Jul. 24, 2002

(65) Prior Publication Data

US 2004/0034381 A1 Feb. 19, 2004

(51) Int. Cl.[7] .............................................. B23B 31/10
(52) U.S. Cl. ..................................... 279/4.09; 279/134
(58) Field of Search ............................. 279/4.09, 4.07, 279/4.06, 37, 43, 50, 57, 134, 135

(56) References Cited

U.S. PATENT DOCUMENTS

| | | | | |
|---|---|---|---|---|
| 2,438,999 A | * | 4/1948 | Hartley et al. ............... 72/20.3 |
| 2,477,773 A | * | 8/1949 | Soussloff et al. ........... 279/4.09 |
| 2,655,384 A | * | 10/1953 | Peterson .................... 279/4.04 |
| 2,788,979 A | * | 4/1957 | Skillin ....................... 279/4.08 |
| 3,072,416 A | * | 1/1963 | Leifer ....................... 279/4.09 |
| 3,861,252 A | * | 1/1975 | Stoffels et al. ................ 82/165 |
| 4,141,564 A | * | 2/1979 | Peden et al. ................ 279/4.12 |
| 4,296,658 A | * | 10/1981 | Champeau et al. ........... 82/147 |
| 4,317,577 A | * | 3/1982 | Cameron .................. 279/2.07 |
| 4,423,880 A | * | 1/1984 | Kosmowski ............... 279/4.07 |
| 4,604,009 A | * | 8/1986 | Tennerstedt ................ 409/233 |
| 4,690,415 A | * | 9/1987 | Holdridge .................. 279/4.09 |
| 4,791,841 A | * | 12/1988 | Pruvot et al. ................ 82/147 |
| 4,945,819 A | * | 8/1990 | Rohm ........................ 92/13.1 |
| 4,957,398 A | * | 9/1990 | Schneider et al. .......... 409/136 |
| 5,026,965 A | | 6/1991 | Ohe et al. ................. 219/121.7 |
| 5,039,261 A | * | 8/1991 | Takada ...................... 409/136 |
| 5,221,098 A | * | 6/1993 | Ayzenshtok et al. ........ 279/4.07 |
| 5,221,824 A | | 6/1993 | Saeda et al. ............ 219/121.82 |
| 5,514,154 A | | 5/1996 | Lau et al. ................... 623/1.15 |
| 5,524,909 A | * | 6/1996 | Wyatt ......................... 279/50 |
| 5,744,778 A | | 4/1998 | Kash et al. ............. 219/121.67 |
| 5,759,192 A | | 6/1998 | Saunders .................... 606/194 |
| 5,780,807 A | | 7/1998 | Saunders ............... 219/121.71 |
| 5,855,377 A | * | 1/1999 | Murphy ...................... 279/50 |
| 5,906,759 A | | 5/1999 | Richter .................. 219/121.63 |
| 5,922,005 A | | 7/1999 | Richter ...................... 606/192 |
| 6,114,653 A | | 9/2000 | Gustafson .............. 219/121.72 |
| 6,131,266 A | | 10/2000 | Saunders ..................... 29/557 |
| 6,197,048 B1 | | 3/2001 | Richter ...................... 623/1.15 |
| 6,257,122 B1 | * | 7/2001 | Michler et al. ................ 92/86 |
| 6,663,548 B2 | * | 12/2003 | Mochida et al. ............. 483/31 |

FOREIGN PATENT DOCUMENTS

JP          58056712 A     *  4/1983    ........... B23B/31/20

* cited by examiner

Primary Examiner—Daniel W. Howell
(74) Attorney, Agent, or Firm—Vida, Arrett & Steinkraus, P.A.

(57) ABSTRACT

A rotary assembly for use in processing a tubular member wherein the assembly comprises a gripping mechanism, that is moveable from an open position to a closed position. In the closed position the gripping mechanism engages at least a portion of the tubular member. The gripping mechanism is operatively engaged to a piston that is fluid actuatable from a first position to a second position by a fluid acting upon the piston, such that when the piston is in the first position the gripping mechanism is in the closed position and when the piston is in the second position the gripping mechanism is in the open position. The assembly defines a circuit through which the fluid is transmitted to the piston.

4 Claims, 5 Drawing Sheets

LOW MASS ROTARY MOTOR ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts, bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Stents have been formed from wire, tube stock, etc. Stents have also been made from sheets of material which are rolled.

A number of techniques have been suggested for the fabrication of stents and other tubular members from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter. Other references wherein laser cutting of stents is described include: U.S. Pat. No. 5,514,154; U.S. Pat. No. 5,759,192; U.S. Pat. No. 6,131,266 and U.S. Pat. No. 6,197,048.

In some instances, stents are tubular members that have been provided with a pattern of apertures or holes cut around the circumference of the tube along most of its length. The resulting stent is utilized to reinforce the walls of the artery or other body lumen to reinforce or prevent closing of the artery or lumen, or to at least prolong the time the artery takes to re-close. The pattern in a stent is typically cut or etched by a mechanical, chemical or laser cutting device.

In manufacturing stents, basic lathe techniques have been adapted to support the tubing used to form the stent during the hole cutting process. Some examples of such techniques and apparatuses used for implementing them are described in U.S. Pat. No. 5,026,965; U.S. Pat. No. 5,221,824; U.S. Pat. No. 5,744,778 and U.S. Pat. No. 6,114,653.

Typically, a piece of tubing is supported between a drive mechanism and a tail stock support in the manner of a lathe. A laser cutting tool positioned above the tubing will cut the pattern by moving relative to the tubing along the length of the finished stent, the tubing being rotated as necessary to present different parts of the circumference to the laser cutting tool.

This manufacturing method has various limitations which results in a fairly high scrap rate. For example, because the pattern typically occupies a large percentage of the surface area of the stent, the stent may sag or bow downwardly during the cutting process as the pattern is cut and the cut area becomes larger. This is particularly true for thin walled material of the type most desirably used to form stents. Accordingly, many stents are rejected as failing to meet the necessary cut accuracy when manufactured by the methods used prior to this invention.

Another limitation that some prior stent manufacturing processes are affected by is that many of the lathe or other rotary systems used in machining the stent tube often employ a live spindle bearing assembly that exits a rotary motor of significant mass. Such assemblies further include a head stock or collet closer having draw bar riding inside a set of ball bearings. A collet is attached to the draw bar and is actuated by a yoke mechanism, which in turn retracts the draw bar into a tapered sleeve. It is clear that such high mass assemblies and their associated components are prone to wear induced complications that may ultimately lead to an increased chance of partial or even complete system failure. Such degradation is implicitly related to the high cost of maintaining such systems.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention addresses limitations of prior tube machining systems by providing a novel rotary assembly having a substantially lower mass and more efficient design than previous designs.

The present invention is directed to several embodiments. In at least one embodiment the invention is directed to a rotary drive assembly having a fluid delivery tubes or lumen for actuating a tube gripping collet or other retaining mechanism. In at least one embodiment, the rotary shaft of the motor or other rotary apparatus is machined or manufactured to include one or more fluid delivery tubes extending longitudinally through the shaft wall. In use, fluid is delivered from a first stationary stage of the apparatus through a rotatable second stage and then servo coupling connection into the shaft. At the distal end of the shaft the tubes are in fluid communication with a collet. Fluid is delivered through the tubes to actuate the collet or other gripping mechanism (s), the actuated gripping mechanism(s) retain an end of a tube that is to be rotated during stent processing by a laser or other etching or cutting device(s).

In at least one embodiment the drive assembly includes a head stock that includes a piston mechanism for opening and closing (actuating) the collet or other gripping mechanism. The piston mechanism is in fluid communication with the fluid delivery tubes and is actuated by fluid flow therefrom.

In at least one embodiment the collet or gripping mechanism is constructed and arranged to be longitudinally driven by the fluid flow to engage the end of a tubular member.

In at least one embodiment the gripping mechanism is an actuating collet, iris, chuck, touhy-borst, elastomer-clamping device or any other device or mechanism that is fluid actuatable for removably engaging a tubular member.

In some embodiments the tubular member is a, member suitable for use in the construction of a stent. In at least one embodiment the tubular member may be a member suitable for use in the construction of a catheter or a component thereof.

In at least one embodiment the tubular member is disposed about a mandrel, wherein the mandrel provides the tubular member with internal support to prevent damage to the tubular member when it is engaged by the gripping mechanism.

In at least one embodiment the rotary shaft of the drive assembly defines a central lumen for transmitting fluid through the drive assembly wherein the fluid is allowed to pass through and/or around the tubular member engaged to the gripping mechanism.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
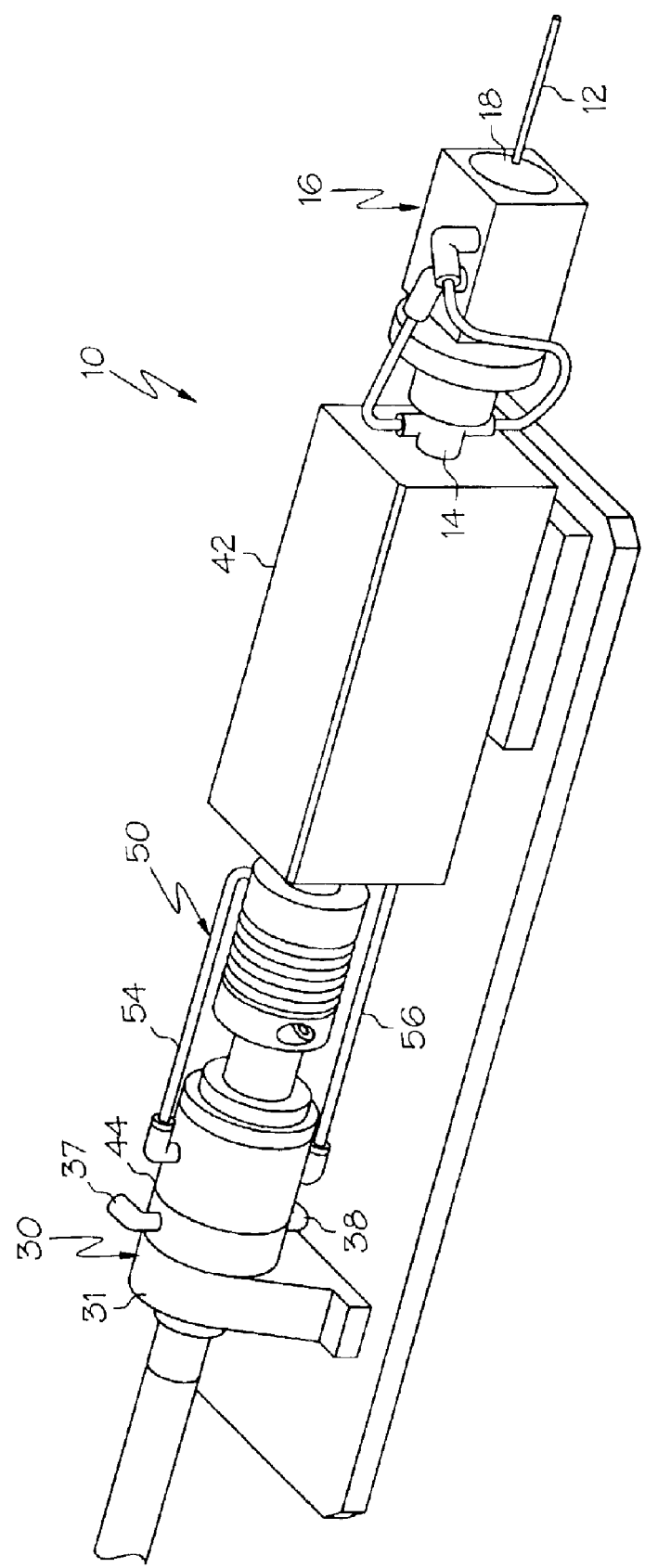
FIG. 1 is a perspective view of an embodiment of the invention.
Figure 2:
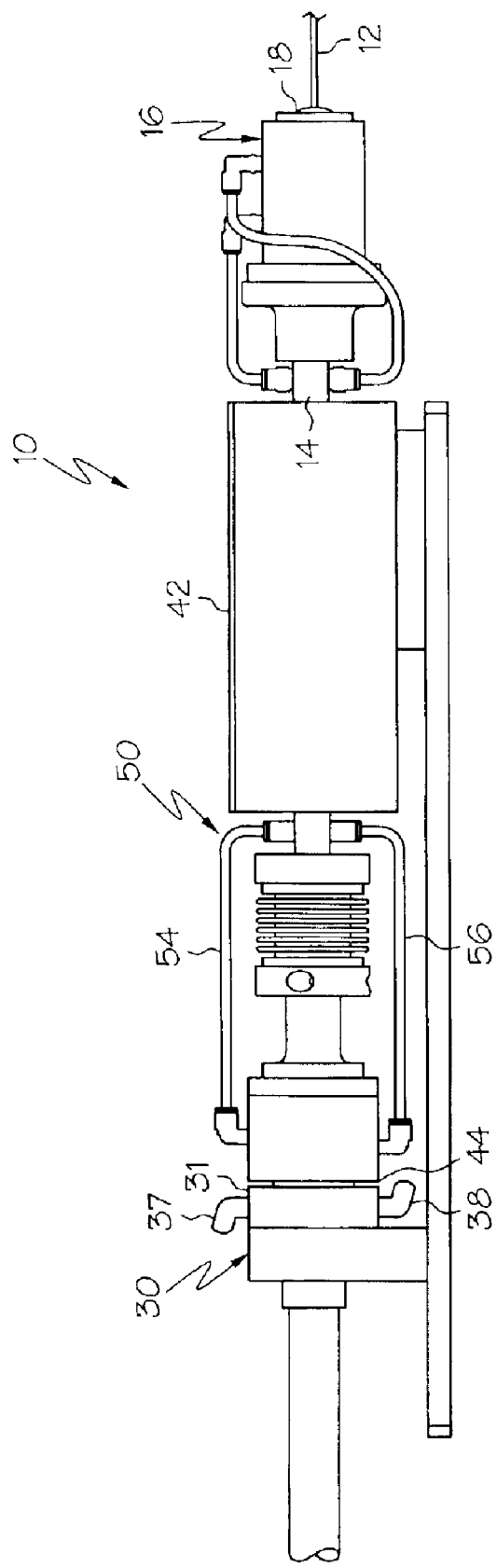
FIG. 2 is a side view of the embodiment shown in FIG. 1.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, the present invention may be embodied in several forms. For example, in FIG. 1 an embodiment of the invention is shown that comprises a rotary assembly, indicated generally at 10, for use in cutting, etching, or otherwise processing a tubular member 12.

Rotary assembly 10 comprises a rotary shaft 14, which at its distal end 16 includes a gripping mechanism 18 that is configured to removably engage at least a portion of the tubular member 12.

In use, rotary assembly 10 acts to grip and rotate the tubular member 12 in a desired manner during the machining process of the tubular member 12.

Typically, tubular member 12 is a hollow tubular member of at least partial metallic composition such as may be suitable for use in the construction of a stent, stent-graft, graft, vena-cava filter or other implantable medical device. In some embodiments the tubular member 12 may be constructed in whole or in part of one or more polymer materials. In these later embodiments the tubular member 12 may be suitable for use in the manufacture of stents and other implantable medical devices, hypo-tubes, catheter shafts, sleeves, and/or other catheter components.

Typically rotary assembly 10 is used in conjunction with, or is apart of a system for cutting or otherwise machining or processing the tubular member 12. For example, in a stent manufacturing process a laser or other cutting mechanism is used to cut or etch a pattern of one or more indentations or holes into the tubular member 12. The rotary assembly 10 retains and rotates the tubular member 12 relative to the cutting mechanism permitting cuts to be made according to a predetermined pattern.

In the embodiments described herein the gripping mechanism 18 may be any type of gripping mechanism, including but not limited to: a collet, iris, chuck, touhy-borst, elastomer-clamping device, etc. The gripping mechanism 18 is engaged to the distal end 16 of the rotary shaft 14 as is shown in FIGS. 1–3 and 5.

Figure 3:
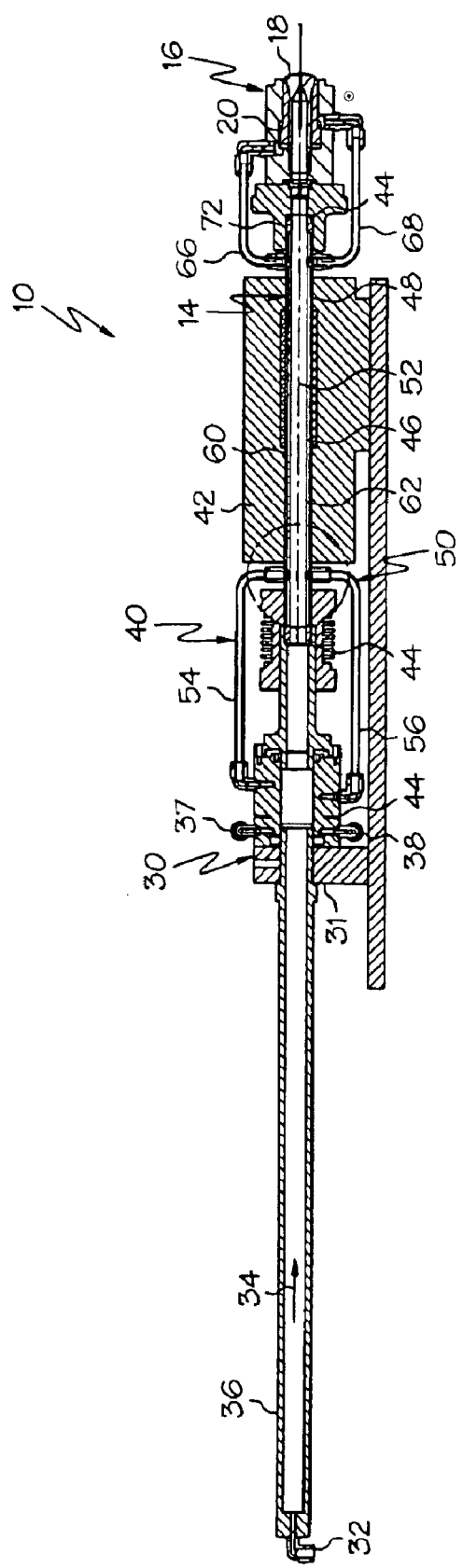
FIG. 3 is a cross-sectional side view of the embodiment shown in FIG. 2.

In the embodiments shown wherein, the gripping mechanism 18 is actuatable between a closed gripping position, wherein at least a portion of the tubular member 12 is retained, and an open gripping position, shown in FIG. 3, wherein the tubular member 12 is released.

The particular mechanism that the assembly 10 employs to actuate the gripping mechanism 18 is a piston 20 or other fluid driven mechanism that actuates longitudinally to the closed position when fluid is applied to the piston 20. The gripping mechanism is moved to the open position when fluid pressure is removed, thereby allowing the piston 20 and gripping mechanism 18 to actuate back toward the shaft 14 thereby releasing the tubular member 12.

Figure 4:
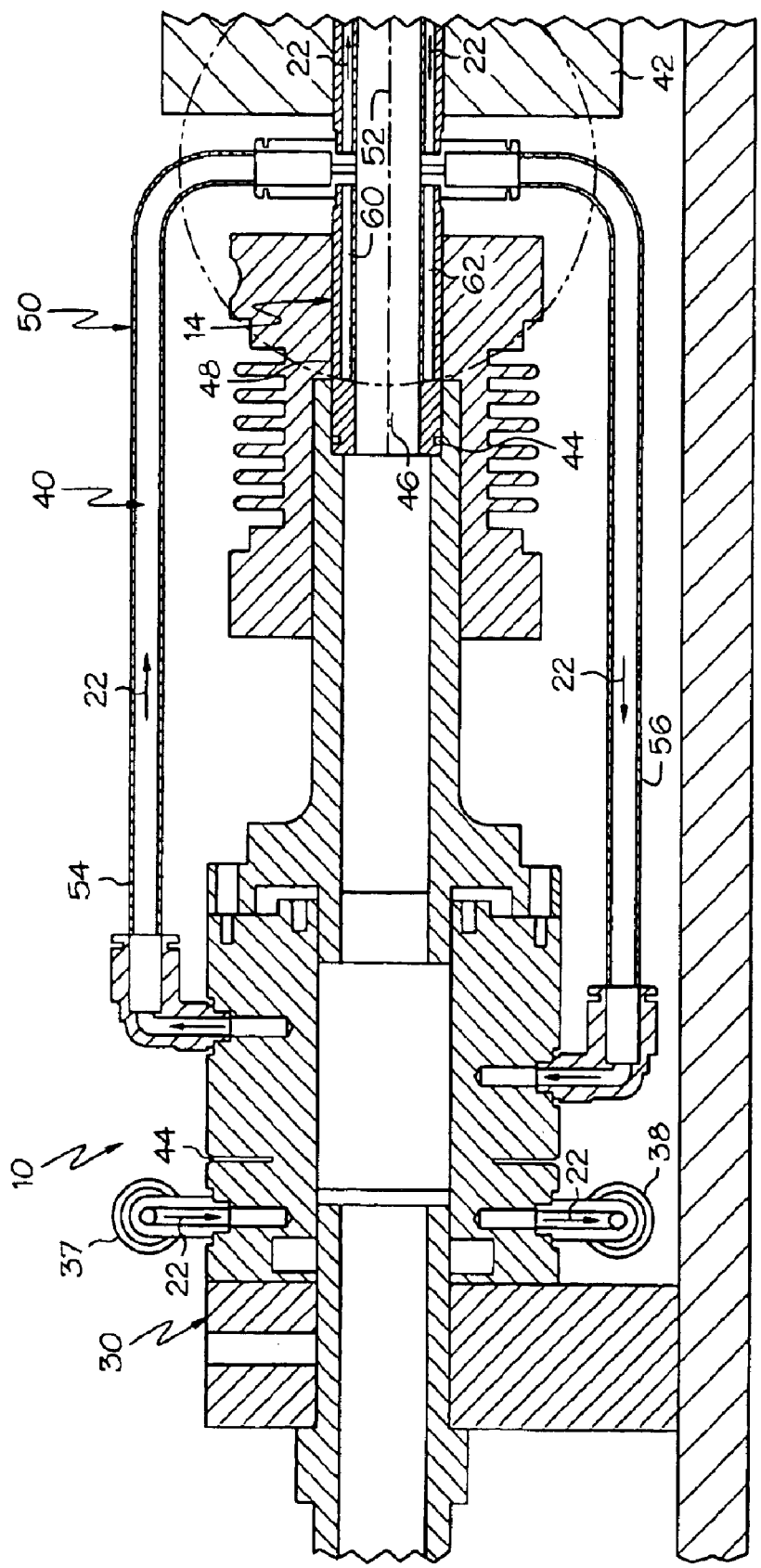
FIGS. 4 and 5 are detailed sectional views of the embodiment shown in FIG. 3 illustrating the prospective flow path for the collet actuating fluid.
Figure 5:
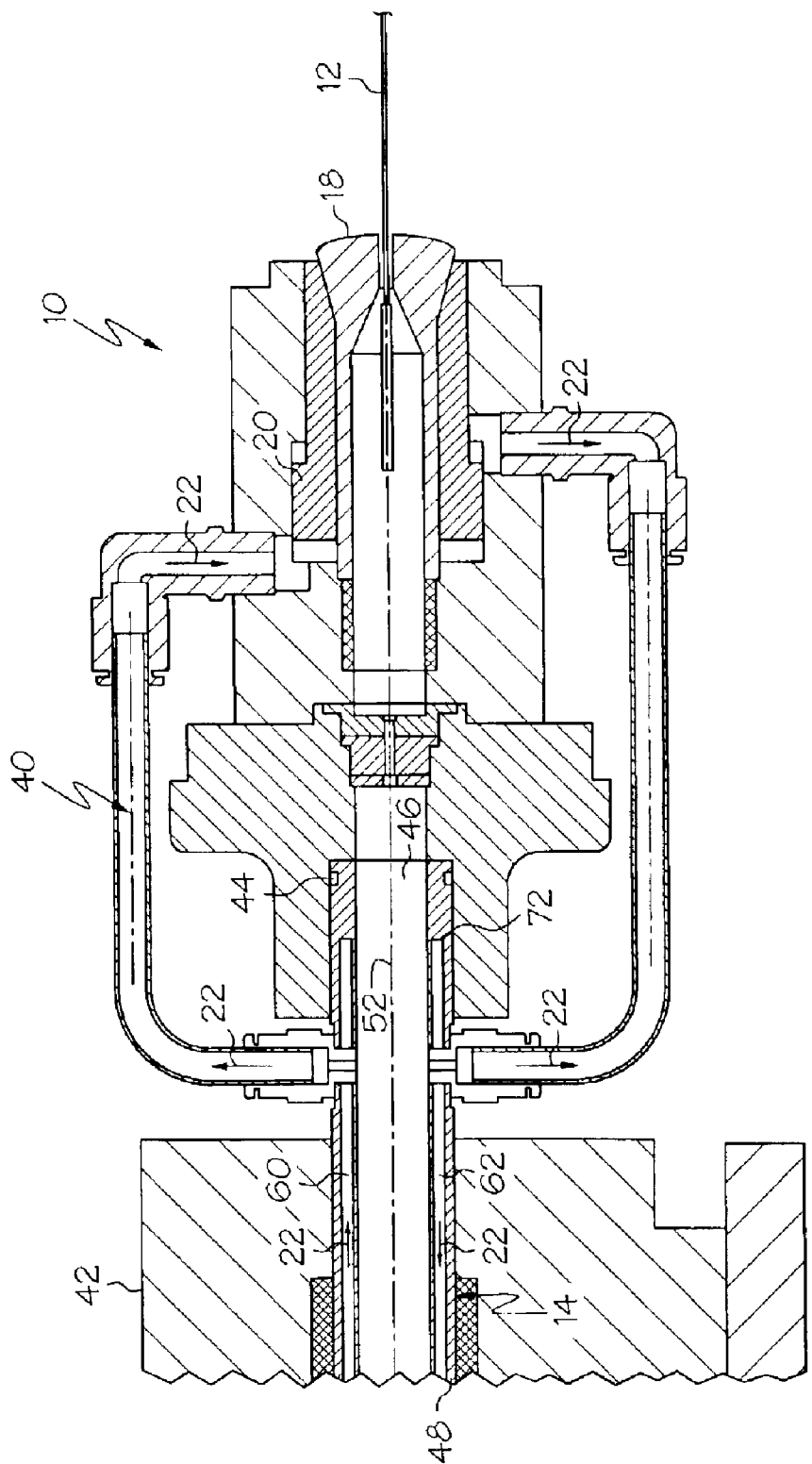

Fluid, indicated by arrow 22 as shown in FIGS. 4 and 5, is transmitted to the piston 20 through a unique series of connected passages defining a fluid circuit 40 such as is described below.

Fluid 22 may be any type of fluid suitable for performing pneumatic or any other type of actuation. For example, fluid 22 may be a gas such as air, oxygen, $CO_2$, etc. In some embodiments fluid 22 may be a liquid such as water, hydraulic fluid, oil, or any other solution, mixture, or composition.

In the embodiments shown in the various FIGS. 1–5, the assembly 10 may be considered as having two primary regions or stages. The first stage 30 defines the fixedly mounted components of the assembly 10, and the second stage 50 are those interconnected components that are moveable relative to the first stage 30.

First stage 30 includes a fluid input 32 for injecting water, air or other fluid, indicated by arrow 34, into a jacket 36. Fluid 34 maybe the same or different as fluid 22. Fluid 34 acts to cool the assembly 10 and may be used to aid in the processing of the tubular member 12.

First stage 30, further includes a housing 31 to which an input fitting 37 and an output fitting 38 are attached. Input fitting 37 defines the initial portion of the circuit 40, wherein fluid 22 is initially injected into the assembly 10. Likewise, output fitting 38 defines the end of lumen circuit 40, wherein fluid 22 leaves the assembly 10.

As indicated above, first stage 30 is stationary relative to the second stage 50, second stage 50 is engaged to the rotary shaft 14 and rotates about the longitudinal axis 52 as shaft 14 is rotated. Shaft 14 is rotated by a servo motor 42 which is disposed about the shaft 14. An o-ring or other seal mechanism 44 separates first stage 30 from second stage 50. However, the second stage 50, employs a first input coupling 54 and a first output coupling 56 that further defines fluid circuit 40 and which are in fluid communication with input fitting 37 and output fitting 38 respectively.

First input coupling 54 and first out put coupling 56 are both distally engaged to the rotary shaft 14 at areas respectively adjacent to the servo motor 42.

As is shown in FIG. 3, the rotary shaft 14 may be a solid or hollow tube. In the embodiments shown, the shaft 14 is a hollow tubular member having a central lumen 46 defined by a shaft wall 48. The shaft wall 48 includes a pair of longitudinal fluid passageways 60 and 62 that further define circuit 40. First input coupling 54 is engaged to passageway 60 and first output coupling 56 is engaged to passageway 62. By employing this unique arrangement of components and passageways the rotary shaft 14 is capable of transmitting fluid 22 longitudinally therethrough in two directions simultaneously. Where shaft 14 is engaged to the second stage 50 a second sealant mechanism 44 is employed to prevent loss of fluid 22.

Where shaft 14 distally exits the servo motor 42, a portion of the shaft 14 is engaged to a second input coupling 66 and a second output coupling 68. The couplings 66 and 68 define lumens that form part of circuit 40. The second input coupling 66 is proximally engaged to the passage 60, whereas second output coupling 68 is proximally engaged to the passage 62. An o-ring or other sealant mechanism 44 prevents fluid loss.

As is shown in the various figures, particularly FIGS. 4 and 5, the fluid circuit 40 that is defined by the various fittings 37 and 38; couplings 54, 56, 66, and 68; and passageways 60 and 62 is a continuous circuit of interconnected passageways or lumens that allows fluid 22 to be transmitted through the assembly 10 to the piston 20. When fluid is injected into the circuit 40 through the input fitting 37, the fluid 22 is transmitted through the first coupling 54, into passage 60 of the rotary shaft 14, and into the second coupling 66. When the fluid 22 exits second coupling 66, the fluid 22 will act upon piston 20 by pushing the piston in longitudinally outward direction from the assembly 10, thereby causing the gripping mechanism 18 to close about the tubular member 12. When the flow of fluid 22 to the piston 20 is interrupted, the piston 20 moves longitudinally toward the assembly 10 to relax gripping mechanism 18 and release the tubular member 12.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A rotary assembly for use in processing a tubular member, the assembly comprising;

a gripping mechanism, the gripping mechanism being moveable from an open position to a closed position, in the closed position the gripping mechanism constructed and arranged to retainingly engage at least a portion of the tubular member;

a piston, the gripping mechanism is operatively engaged to the piston, the piston being fluid actuatable from a first position to a second position by a fluid acting upon the piston, such that when the piston is in the first position the gripping mechanism is in the closed position and when the piston is in the second position the gripping mechanism is in the open position, the assembly defining a circuit through which the fluid is transmitted to the piston;

a rotary shaft, the rotary shaft being rotatable about a longitudinal axis, a portion of the rotary shaft being operatively engaged to a motor and a first end portion of the rotary shaft being operatively engaged to the piston, the rotary shaft defining a first fluid transmission lumen and a second fluid transmission lumen;

a housing, the housing having a fixed position relative to the rotary shaft, the housing comprising a fluid input port and a fluid output port;

a first fluid transmission coupling extending externally from the housing to the rotary shaft, the first fluid transmission coupling defining a first fluid transmission coupling lumen which extends between and is in fluid communication with the fluid input port and the first fluid transmission lumen; and a second fluid transmission coupling extending externally from the housing to the rotary shaft, the second fluid transmission coupling defining a second fluid transmission coupling lumen which extends between and is in fluid communication with the fluid output port and the second fluid transmission lumen, the circuit being comprised of the fluid input port, the first fluid transmission coupling lumen, first fluid transmission lumen, the second fluid transmission lumen, the second fluid transmission coupling lumen, and the fluid output port.

2. The rotary assembly of claim 1 further comprising a third fluid transmission coupling and a fourth fluid transmission coupling, the third fluid transmission coupling having a first end and a second end and defining a lumen therebetween, the first end being fluidly engaged to the first fluid transmission lumen, the second end being fluidly engaged to the piston, the fourth fluid transmission coupling having a first end and a second end and defining a lumen therebetween, the first end being fluidly engaged to the second fluid transmission lumen, the second end being fluidly engaged to the piston, the circuit further comprising the lumen defined by the third fluid transmission coupling and the lumen defined by the fourth fluid transmission coupling.

3. A rotary assembly for processing a tubular member, the assembly comprising:

a gripping mechanism, a rotary shaft operatively engaged to the gripping mechanism, and a plurality of fluid conduits, wherein two of the fluid conduits are defined by the rotary shaft, and at least two other fluid conduits are positioned externally from the rotary shaft and the gripping mechanism but provide fluid communication therebetween the gripping mechanism being fluid actuated to move the gripping mechanism between a closed position and an open position, in the closed position the gripping mechanism constructed and arranged to engage at least a portion of a tubular member.

4. A rotary assembly for processing a tubular member, the assembly comprising:

a fluid actuatable gripping mechanism for removably engaging at least a portion of a tubular body, wherein the fluid actuatable gripping mechanism is operatively engaged to two fluid lumens each being defined by a lumen conduit positioned external to the gripping mechanism, each lumen conduit being engaged to a rotatable shaft adjacent to the gripping mechanism, the rotatable shaft defines a first transmission lumen in fluid communication with one of the two fluid lumens and a second transmission lumen in fluid communication with the other of the two fluid lumens.

* * * * *